United States Patent
VanderDussen et al.

(10) Patent No.: US 9,101,132 B2
(45) Date of Patent: Aug. 11, 2015

(54) DISPENSER COMPRISING A POLYESTER MEMBRANE FOR CONTROL OF MITES IN BEE HIVES

(75) Inventors: David VanderDussen, Ontario (CA); Renate Wapenhensch, Speyer (DE); Markus Gewehr, Kastellaun (DE); Marco Candolfi, Nusshof (CH); Roland Becker, Haβloch (DE); Sandrine Leblond, Bessenay (FR); Jean-Marc Petat, Chazay (FR); Nicole Hanewald, Limburgerhof (DE); Tobias Huth, Raleigh, NC (US)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/395,142

(22) PCT Filed: Sep. 1, 2010

(86) PCT No.: PCT/EP2010/062776
§ 371 (c)(1),
(2), (4) Date: Mar. 9, 2012

(87) PCT Pub. No.: WO2011/029754
PCT Pub. Date: Mar. 17, 2011

(65) Prior Publication Data
US 2012/0171268 A1    Jul. 5, 2012

Related U.S. Application Data

(60) Provisional application No. 61/241,975, filed on Sep. 14, 2009, provisional application No. 61/348,753, filed on May 27, 2010.

(51) Int. Cl.
*A01N 25/00* (2006.01)
*A01N 37/02* (2006.01)

(52) U.S. Cl.
CPC .................................... *A01N 37/02* (2013.01)

(58) Field of Classification Search
None
See application file for complete search history.

(56) References Cited

U.S. PATENT DOCUMENTS

| | | | |
|---|---|---|---|
| 6,037,374 A | 3/2000 | Kochansky et al. | |
| 6,159,489 A | 12/2000 | Sakurada et al. | |
| 6,646,014 B2 | 11/2003 | Watkins | |
| 2003/0060542 A1* | 3/2003 | Witt et al. | 524/35 |
| 2006/0008492 A1* | 1/2006 | Janowicz et al. | 424/405 |
| 2007/0059333 A1* | 3/2007 | Volby | 424/410 |
| 2008/0274885 A1 | 11/2008 | Martin et al. | |

FOREIGN PATENT DOCUMENTS

| | | |
|---|---|---|
| CA | 2 237 484 | 11/1998 |
| EP | 1 493 332 | 1/2005 |
| WO | WO 97/47193 | 12/1997 |
| WO | WO 02/30181 | 4/2002 |
| WO | WO 2006/017310 | 2/2006 |
| WO | WO 2007/074042 | 7/2007 |
| WO | WO 2010/064013 | 6/2010 |

OTHER PUBLICATIONS

Barinov, "Composition for protecting honey bees from parasite mites", RU 2222189, Jan. 27, 2004, Database WPI, Week 200416.
Daniels et al., "Membrane-barrier delivery of formic acid, a chemical used for mite control on honey bees (*Apis mellifera*)", Journal of Agricultural Research, vol. 38, 1999, pp. 63-69.
Eguaras et al., "A New Product with Formic Acid for *Varroa jacobsoni* Oud. Control in Argentina. I. Efficacy", J. Vet. Med. B., vol. 48, 2001, pp. 11-14. Search Report.
Kochansky et al., "Development of a Gel Formulation of Formic Acid for Control of Parasitic Mites of Honey Bees", J. Agric. Food Chem., vol. 47, 1999, pp. 3850-3853. Search Report.
International Search Report, PCT/EP2010/062776, Oct. 11, 2011.
International Preliminary Report on Patentability, PCT/EP2010/062776, May 3, 2011.

* cited by examiner

*Primary Examiner* — Dennis J Parad
(74) *Attorney, Agent, or Firm* — Brinks Gilson & Lione

(57) ABSTRACT

The present invention is related to a dispenser, which is filled with a gel comprising a C1 to C10 carboxylic acid and a thickener, comprising a polyester membrane. The invention further relates to said gel. It also relates to s method for preparing said dispenser, comprising a) mixing C1 to C10 carboxylic acid and the thickener, and b) filling the mixture of step a) into the dispenser. The invention further relates to a method for the control of mites in bee hives comprising putting said dispenser inside or near a bee hive. It also relates to a use of the dispenser or the gel for the control of mites or of nosema in agricultural, industrial or domestic environment.

21 Claims, No Drawings

DISPENSER COMPRISING A POLYESTER MEMBRANE FOR CONTROL OF MITES IN BEE HIVES

This application is a National Stage application of International Application No. PCT/EP2010/062776 filed Sep. 1, 2010, which claims the benefit of U.S. Provisional Application No. 61/241,975, filed Sep. 14, 2009, and U.S. Provisional Application No. 61/348,753, filed May 27, 2010, the entire contents of which are hereby incorporated herein by reference.

The present invention is related to a dispenser, which is filled with a gel comprising a $C_1$ to $C_{10}$ carboxylic acid and a thickener, comprising a polyester membrane. The invention further relates to said gel. It also relates to s method for preparing said dispenser, comprising a) mixing $C_1$ to $C_{10}$ carboxylic acid and the thickener, and b) filling the mixture of step a) into the dispenser. The invention further relates to a method for the control of mites in bee hives comprising putting said dispenser inside or near a bee hive. It also relates to a use of the dispenser or the gel for the control of mites in agricultural, industrial or domestic environment. Combinations of preferred embodiments with other preferred embodiments are within the scope of the present invention Various dispensers of organic acids for the control of mites in bee hives are well known:

Kochansky and Shimanuki, Journal of Agri. Food Chem. 1999, 47, 3850-3853 disclosed gel formulations of formic acid for control of parasitic mites of honey bees. Various gelling agents were disclosed, such as fumed silica, polyacrylic acid, xanthan gum, guar gum, gum acacia, bentonite clay or starch-graft polymers. As a dispenser, prefilled packets made of polyethylene, polypropylene, polyethylene/polyester laminate, Barex film (typically a modified acrylonitrile-methyl acrylate copolymer), or Valeron/Surlyn (the latter is typically a partially neutralized ethylene methacrylic acid copolymers) were used. For dispensing the formic acid, four slits were cut into the dispenser.

U.S. Pat. No. 6,037,374 discloses a dispenser for the treatment of parasitic mites of honey bees, which comprises a gel composition of formic acid and a gelling agent selected from fumed silica and polyacrylic acid. As dispenser polyethylene bags were used, in which four slits were cut for dispensing. Perforated containers were also suggested.

Daniels et al., Journal of Apicultural Research 1999, 38, 63-69 disclose a membrane-barrier delivery of formic acid for mite control on honey bees. As membrane devices latex condoms were used with a membrane thickness of 71 to 650 µm.

WO 2002/30181 discloses a treatment fluid dispenser comprising a foam core having capillary cell structure, which is encased in a fluid impervious skin. When the foam core is cut in a half and saturated with formic acid, it may be vertically hung in the bee space so as to downwardly dispose on an exposed surface of the foam core. Thus, formic acid is evaporated.

WO 1997/47193 discloses a slow release gel formulation for the control of infestations in bee hives, comprising an essential oil or organic acid. The gel may be in the form of a shallow tray dispenser with a hermetically sealing lid, e.g. made of aluminium or plastic foil.

These known devices are associated with various disadvantages, which should be overcome be the present invention. Thus, it was an object of the present invention was to find a device for improving the health of bee colonies, which would allow an easy and reliable treatment: It should be easy for the beekeeper to handle the device, especially without coming into contact with the active ingredients, such as corrosive formic acid. The dispensing of the active ingredient should be reliable at various climate conditions, for example also in warmer climates in southern USA or California. All of the formulation additives should be non-toxic to the bees, preferably including the dispenser. The dispenser and the formulation should be biodegradable.

The object was solved by a dispenser, which is filled with a gel comprising a $C_1$ to $C_{10}$ carboxylic acid and a thickener, comprising a polyester membrane.

The dispenser comprises a polyester membrane. Such a dispenser may dispense the gel to the environment by the polyester membrane. The dispenser may have any three-dimensional hollow form, which is suitable to contain a gel, such as a cylindrical, spherical, cuboid, or like a pouch. The dispenser may be made of any dispenser material, for example metal, plastic, paper, glass or wood, preferably plastic. Typically, the dispenser material is stable towards formic acid. The dispenser material may be permeable for formic acid vapour. The dispenser is filled with the gel. Usually, at least 50%, preferably at least 80% of the inner volume of the dispenser is filled with the gel. There might be some air inside for example.

A part of the dispenser hollow form may comprise the membrane. For example, the base of a cylinder made of dispenser material could be made of the polyester membrane; or one side of a cube made of dispenser material may be made of the polyester membrane. Usually, the polyester membrane covers at least 10% of the surface of the dispenser. Preferably, the membrane covers at least 30%, more preferably at least 50%, and most preferably at least 95% of the surface of the dispenser. In a especially preferred embodiment the dispenser is a pouch made of the membrane. For example the polyester membrane forms a pouch, which may be filled with the gel. Usually, this pouch has a volume of 5 to 5000 ml, preferably 30 to 1000 ml, more preferably 80 to 300 ml.

The polyester membrane has typically a thickness of 3 to 500 µm, preferably 10 to 200 µm, more preferably 20 to 150 µm, and even more preferably 20 to 120 µm. The membrane may be composed of at least one layer, for example one, two or three layers. Often, the layers comprise various processing additives, such as antiblocking or antislipping additives, which are well known in the art. Preferably, all layers, which are present in the membrane, are made of a polyester, preferably of a semiaromatic polyester.

The membrane may be produced by common film extrusion methods.

The polyester membrane may be attached to a coating substrate. Typically, the coating substrate is coated with the polyester, forming a laminate. Preferred coating substrates are those which are compostable or rot, such as moldings of paper, cellulose or starch. Preferably, the coating substrate is paper or cellulose. The polyester membrane can be attached to the coating substrate by rolling, spreading, spraying or pouring. A preferred coating process is described in EP08165372.7 filed on 29.9.2008 and in EP09010388.8 filed on 12.8.2009, which are both enclosed herein by reference.

The polyester membrane comprises usually a polyester. Polyesters are well known polymers. They comprises monomers in polymerized form, such as diols and diacids (or diesters), or hydroxyacids (or hydroxyesters). Preferably, the polyester is an aliphatic or semiaromatic polyester, more preferably a semiaromatic polyester.

Suitable polyester are aliphatic polyester. These include homopolymers of aliphatic hydroxycarboxylic acids or lactones, and also copolymers or block copolymers of different hydroxycarboxylic acids or lactones or mixtures of these. These aliphatic polyesters may also contain units of diols and/or of isocyanates. The aliphatic polyesters may also contain units which derive from tri- or polyfunctional compounds, for example from epoxides, from acids or from triols. The aliphatic polyesters may contain the latter units as individual units, or a number of these, possibly together with the diols and/or isocyanates. Processes for preparing aliphatic polyesters are known to the skilled worker. In preparing the aliphatic polyesters it is, of course, also possible to use mixtures made from two or more comonomers and/or from other units, for example from epoxides or from polyfunctional aliphatic or aromatic acids, or from polyfunctional alcohols. The aliphatic polyesters generally have molar asses (number-average) of from 10,000 to 100,000 g/mol.

Examples of aliphatic polyesters are polymeric reaction products of lactic acid, poly-3-hydroxybutanoates, or polyesters built up from aliphatic or cycloaliphatic dicarboxylic acids and from aliphatic or cycloaliphatic diols. The aliphatic polyesters may also be random or block copolyesters which contain other monomers. The proportion of the other monomers is generally up to 10 percent by weight. Preferred comonomers are hydroxycarboxylic acids or lactones or mixtures of these.

Polymeric reaction products of lactic acid are known per se or may be prepared by processes known per se. Besides polylactide, use may also be made of those copolymers or block copolymers based on lactic acid with other monomers. Linear polylactides are mostly used. However, branched lactic acid polymers may also be used. Examples of branching agents are polyfunctional acids or alcohols. Polylactides which may be mentioned as an example are those obtainable essentially from lactic acid or from its C1-C4-alkyl esters or mixtures of these, with at least one aliphatic C4-C10 dicarboxylic acid and with at least one C3-C10 alkanol having from three to five hydroxyl groups.

Poly-3-hydroxybutanoates are homopolymers or copolymers of 3-hydroxybutanoic acid or mixtures thereof with 4-hydroxybutanoic acid and with 3-hydroxyvaleric acid, in particular with a proportion by weight of up to 30 percent, preferably up to 20 percent, of the last-named acid. Suitable polymers of this type also include those with R-stereo-specific configuration. Polyhydroxybutanoates or copolymers of these can be prepared microbially. Processes for the preparation from various bacteria and fungi are known as well as a process for preparing stereospecific polymers. It is also possible to use block copolymers of the above-mentioned hydroxycarboxylic acids or lactones, or of their mixtures, oligomers or polymers.

Polyesters built up from aliphatic or cycloaliphatic dicarboxylic acids and from aliphatic or cycloaliphatic diols are those built up from aliphatic or cycloaliphatic dicarboxylic acids or from mixtures of these, and from aliphatic or cycloaliphatic diols, or from mixtures of these. According to the invention either random or block copolymers may be used. Suitable aliphatic dicarboxylic acids according to the invention generally have from 2 to 10 carbon atoms, preferably from 4 to 6 carbon atoms. They may be either linear or branched. For the purposes of the present invention, cycloaliphatic dicarboxylic acids which may be used are generally those having from 7 to 10 carbon atoms, and in particular those having 8 carbon atoms. However, in principle use may also be made of dicarboxylic acids having a larger number of carbon atoms, for example having up to 30 carbon atoms. Examples which should be mentioned are: malonic acid, succinic acid, glutaric acid, adipic acid, pimelic acid, azelaic acid, sebacic acid, fumaric acid, 2,2-dimethylglutaric acid, suberic acid, 1,3-cyclopentanedicarboxylic acid, 1,4-cyclohexanedicarboxylic acid, 1,3-cyclohexanedicarboxylic acid, diglycolic acid, itaconic acid, maleic acid and 2,5-norbornanedicarboxylic acid, preferably adipic acid. Mention should also be made of ester-forming derivatives of the abovementioned aliphatic or cycloaliphatic dicarboxylic acids, which may likewise be used, in particular the di-C1-C6-alkyl esters, such as dimethyl, diethyl, di-n-propyl, diisopropyl, di-n-butyl, diisobutyl, di-tert-butyl, di-n-pentyl, diisopentyl and di-n-hexyl esters. Anhydrides of the dicarboxylic acids may likewise be used. The dicarboxylic acids or ester-forming derivatives of these may be used individually or as a mixture of two or more of these.

Suitable aliphatic or cycloaliphatic diols generally have from 2 to 10 carbon atoms, preferably from 4 to 6 carbon atoms. They may be either linear or branched. Examples are 1,4-butanediol, ethylene glycol, 1,2- or 1,3-propanediol, 1,6-hexanediol, 1,2- or 1,4-cyclohexanediol or mixtures of these.

Examples of aliphatic polyesters which may be used are aliphatic copolyesters as described in WO 94/14870, in particular aliphatic copolyesters made from succinic acid, from its diesters, or from mixtures with other aliphatic acids or, respectively, diesters, for example glutaric acid and butanediol, or mixtures made from this diol with ethylene glycol, propanediol or hexanediol or mixtures of these. In another embodiment, preferred aliphatic polyesters include polycaprolactone.

According to the invention, the term semiaromatic polyesters refers to polyester, which comprise aliphatic and aromatic monomers in polymerized form. The term semiaromatic polyesters is also intended to include polyester derivatives, such as polyetheresters, polyesteramides, or polyetheresteramides. Among the suitable semiaromatic polyesters are linear non-chain-extended polyesters (WO 92/09654). Preference is given to chain-extended and/or branched semiaromatic polyesters. The latter are disclosed in the specifications mentioned at the outset, WO 96/15173, WO 96/15174, WO 96/15175, WO 96/15176, WO 96/21689, WO 96/21690, WO 96/21691, WO 96/21689, WO 96/25446, WO 96/25448, and WO 98/12242, expressly incorporated herein by way of reference. Mixtures of different semiaromatic polyesters may also be used. In particular, the term semiaromatic polyesters is intended to mean products such as Ecoflex® (BASF Aktiengesellschaft) and Eastar® Bio and Origo-Bi (Novamont).

Among the particularly preferred semiaromatic polyesters are polyesters which comprise the following significant components
A) an acid component composed of
  a1) from 30 to 99 mol % of at least one aliphatic, or at least one cycloaliphatic, dicarboxylic acid, or its ester-forming derivatives, or a mixture of these
  a2) from 1 to 70 mol % of at least one aromatic dicarboxylic acid, or its esterforming derivative, or a mixture of these, and
  a3) from 0 to 5 mol % of a compound comprising sulfonate groups,
  and
B) a diol component selected from at least one $C_2$-$C_{12}$ alkanediol and at least one $C_5$-$C_{10}$ cycloalkanediol, or a mixture of these.

If desired, the semiaromatic polyester may also comprise one or more components selected from C) and D), wherein
C) is a component selected from
  c1) at least one dihydroxy compound comprising ether functions and having the formula I $$HO-[(CH_2)_n-O]_m-H \quad (I)$$

where n is 2, 3 or 4 and m is a whole number from 2 to 250,
  c2) at least one hydroxycarboxylic acid of the formula IIa or IIb

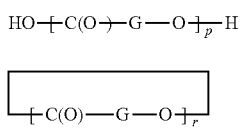
(IIa)

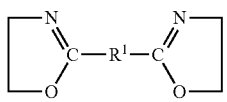
(IIb)

where p is a whole number from 1 to 1500 and r is a whole number from 1 to 4, and G is a radical selected from the group consisting of phenylene, $-(CH_2)_q-$, where q is a whole number from 1 to 5, $-C(R)H-$ and $-C(R)HCH_2-$, where R is methyl or ethyl, c3) at least one amino-$C_2$-$C_{12}$ alkanol, or at least one amino-$C_5$-$C_{10}$ cycloalkanol, or a mixture of these, c4) at least one diamino-$C_1$-$C_8$ alkane, c5) at least one 2,2'-bisoxazoline of the formula III

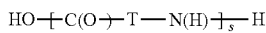
(III)

where $R^1$ is a single bond, a $(CH_2)_z$-alkylene group, where z=2, 3 or 4, or a phenylene group, c6) at least one aminocarboxylic acid selected from the group consisting of the naturally occurring amino acids, polyamides obtainable by polycondensing a dicarboxylic acid having from 4 to 6 carbon atoms with a diamine having from 4 to 10 carbon atoms, compounds of the formulae IVa and IVb

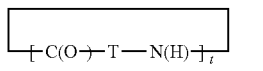
(IVa)

(IVb)

where s is a whole number from 1 to 1500 and t is a whole number from 1 to 4, and T is a radical selected from the group consisting of phenylene, $-(CH_2)_u-$, where u is a whole number from 1 to 12, $-C(R^2)H-$ and $-C(R^2)HCH_2-$, where $R^2$ is methyl or ethyl, and polyoxazolines having the repeat unit V

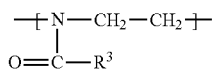
(V)

where $R^3$ is hydrogen, $C_1$-$C_6$-alkyl, $C_5$-$C_8$-cycloalkyl, phenyl, either unsubstituted or with up to three $C_1$-$C_4$-alkyl substituents, or tetrahydrofuryl, or a mixture composed of c1 to c6, and wherein D) is a component selected from d1) at least one compound having at least three groups capable of ester formation, d2) at least one isocyanate, d3) at least one divinyl ether, or a mixture composed of d1) to d3).

In one preferred embodiment, the acid component A of the semiaromatic polyesters comprises from 30 to 70 mol %, in particular from 40 to 60 mol %, of a1, and from 30 to 70 mol %, in particular from 40 to 60 mol %, of a2.

Aliphatic acids and the corresponding derivatives a1 which may be used are generally those having from 2 to 10 carbon atoms, preferably from 4 to 6 carbon atoms. They may be either linear or branched. The cycloaliphatic dicarboxylic acids which may be used for the purposes of the present invention are generally those having from 7 to 10 carbon atoms and in particular those having 8 carbon atoms. In principle, however, it is also possible to use dicarboxylic acids having a larger number of carbon atoms, for example having up to 30 carbon atoms.

Examples which may be mentioned are: malonic acid, succinic acid, glutaric acid, 2-methylglutaric acid, 3-methylglutaric acid, adipic acid, pimelic acid, azelaic acid, sebacic acid, fumaric acid, 2,2-dimethylglutaric acid, suberic acid, 1,3-cyclopentanedicarboxylic acid, 1,4-cyclohexanedicarboxylic acid, 1,3-cyclohexanedicarboxylic acid, diglycolic acid, itaconic acid, maleic acid, brassylic acid, and 2,5-norbornanedicarboxylic acid.

Ester-forming derivatives of the abovementioned aliphatic or cycloaliphatic dicarboxylic acids which may also be used and which may be mentioned are in particular the di-$C_1$-$C_6$-alkyl esters, such as dimethyl, diethyl, di-n-propyl, diisopropyl, di-n-butyl, diisobutyl, di-tert-butyl, di-n-pentyl, diisopentyl or di-n-hexyl esters. It is also possible to use anhydrides of the dicarboxylic acids.

The dicarboxylic acids or their ester-forming derivatives may be used here individually or in the form of a mixture composed of two or more of these.

It is preferable to use succinic acid, adipic acid, azelaic acid, sebacic acid, brassylic acid, or respective ester-forming derivatives thereof, or a mixture of these. It is particularly preferable to use succinic acid, adipic acid, or sebacic acid, or respective ester-forming derivatives thereof, or a mixture of these. It is particularly preferable to use adipic acid or its ester-forming derivatives, for example its alkyl esters, or a mixture thereof. The aliphatic dicarboxylic acid used preferably comprises sebacic acid or a mixture of sebacic acid with adipic acid, if polymer mixtures with "hard" or "brittle" components ii), for example polyhydroxybutyrate or in particular polylactide, are prepared. The aliphatic dicarboxylic acid used preferably comprises succinic acid or a mixture of succinic acid with adipic acid if polymer mixtures with "soft" or "tough" components ii), for example polyhydroxybutyrate-co-valerate, are prepared.

A further advantage of succinic acid, azelaic acid, sebacic acid, and brassylic acid is that they are accessible renewable raw materials.

Aromatic dicarboxylic acids a2 which may be mentioned are generally those having from 8 to 12 carbon atoms and preferably those having 8 carbon atoms. By way of example, mention may be made of terephthalic acid, isophthalic acid, 2,6-naphthoic acid and 1,5-naphthoic acid, and also ester-forming derivatives of these. Particular mention may be made here of the di-$C_1$-$C_6$-alkyl esters, e.g. dimethyl, diethyl, di-n-propyl, diisopropyl, di-n-butyl, diisobutyl, di-tert-butyl, di-n-pentyl, diisopentyl, or di-n-hexyl esters. The anhydrides of the dicarboxylic acids a2 are also suitable esterforming derivatives.

However, in principle it is also possible to use aromatic dicarboxylic acids a2 having a greater number of carbon atoms, for example up to 20 carbon atoms.

The aromatic dicarboxylic acids or ester-forming derivatives of these a2 may be used individually or as a mixture of two or more of these. It is particularly preferable to use terephthalic acid or ester-forming derivatives thereof, such as dimethyl terephthalate.

The compound used comprising sulfonate groups is usually one of the alkali metal or alkaline earth metal salts of a sulfonate-containing dicarboxylic acid or ester-forming derivatives thereof, preferably alkali metal salts of 5-sulfoisophthalic acid or a mixture of these, particularly preferably the sodium salt.

In one of the preferred embodiments, the acid component A comprises from 40 to 60 mol % of a1, from 40 to 60 mol % of a2 and from 0 to 2 mol % of a3. In another preferred embodiment, the acid component A comprises from 40 to 59.9 mol % of a1, from 40 to 59.9 mol % of a2 and from 0.1 to 1 mol % of a3, in particular from 40 to 59.8 mol % of a1, from 40 to 59.8 mol % of a2 and from 0.2 to 0.5 mol % of a3.

The diols B are generally selected from the group consisting of branched or linear alkanediols having from 2 to 12 carbon atoms, preferably from 4 to 6 carbon atoms, or from the group consisting of cycloalkanediols having from 5 to 10 carbon atoms.

Examples of suitable alkanediols are ethylene glycol, 1,2-propanediol, 1,3-propanediol, 1,2-butanediol, 1,4-butanediol, 1,5-pentanediol, 2,4-dimethyl-2-ethyl-1,3-hexanediol, 2,2-dimethyl-1,3-propanediol, 2-ethyl-2-butyl-1,3-propanediol, 2-ethyl-2-isobutyl-1,3-propanediol and 2,2,4-trimethyl-1,6-hexanediol, in particular ethylene glycol, 1,3-propanediol, 1,4-butanediol or 2,2-dimethyl-1,3-propanediol (neopentyl glycol); cyclopentanediol, 1,4-cyclohexanediol, 1,2-cyclohexanedimethanol, 1,3-cyclohexanedimethanol, 1,4-cyclohexanedimethanol or 2,2,4,4-tetramethyl-1,3-cyclobutanediol. Particular preference is given to 1,4-butanediol, in particular in combination with adipic acid as component a1), and 1,3-propanediol, in particular in combination with sebacic acid as component a1). Another advantage of 1,3-propanediol is that it is an available renewable raw material. It is also possible to use mixtures of different alkanediols.

Depending on whether an excess of acid groups or of OH end groups is desired, either component A or component B may be used in excess. In one preferred embodiment, the molar ratio of the components A and B used may be from 0.4:1 to 1.5:1, preferably from 0.6:1 to 1.1:1.

Besides components A and B, the polyesters on which the polyester mixtures of the invention are based may comprise other components.

Dihydroxy compounds c1 which are preferably used are diethylene glycol, triethylene glycol, polyethylene glycol, polypropylene glycol and polytetrahydrofuran (polyTHF), particularly preferably diethylene glycol, triethylene glycol and polyethylene glycol, and mixtures of these may also be used, as may compounds which have different variables n (see formula I), for example polyethylene glycol which comprises propylene units (n=3), obtainable, for example, by using methods of polymerization known per se and polymerizing first with ethylene oxide and then with propylene oxide, and particularly preferably a polymer based on polyethylene glycol with different variables n, where units formed from ethylene oxide predominate. The molar mass ($M_n$) of the polyethylene glycol is generally selected within the range from 250 to 8000 g/mol, preferably from 600 to 3000 g/mol.

In one of the preferred embodiments for preparing the semiaromatic polyesters use may be made, for example, of from 15 to 98 mol %, preferably from 60 to 99.5 mol %, of the diols B and from 0.2 to 85 mol %, preferably from 0.5 to 30 mol %, of the dihydroxy compounds c1, based on the molar amount of B and c1.

In one preferred embodiment, the hydroxycarboxylic acid c2) used is: glycolic acid, D-, L- or D,L-lactic acid, 6-hydroxyhexanoic acid, cyclic derivatives of these, such as glycolide (1,4-dioxane-2,5-dione), D- or L-dilactide (3,6-dimethyl-1,4-dioxane-2,5-dione), p-hydroxybenzoic acid, or else their oligomers and polymers, such as 3-polyhydroxybutyric acid, polyhydroxyvaleric acid, polylactide (obtainable, for example, as NatureWorks® 4042D (NatureWorks) or else a mixture of 3-polyhydroxybutyric acid and polyhydroxyvaleric acid (obtainable from PHB Industrial, Tianan, or Metabolix) and, for preparing semiaromatic polyesters, particularly preferably the low-molecular-weight and cyclic derivatives thereof.

Examples of amounts which may be used of the hydroxycarboxylic acids are from 0.01 to 50% by weight, preferably from 0.1 to 40% by weight, based on the amount of A and B.

The amino-$C_2$-$C_{12}$ alkanol or amino-$C_5$-$C_{10}$ cycloalkanol used (component c3) which for the purposes of the present invention also include 4-aminomethylcyclohexanemethanol, are preferably amino-$C_2$-$C_6$ alkanols, such as 2-aminoethanol, 3-aminopropanol, 4-aminobutanol, 5-aminopentanol or 6-aminohexanol, or else amino-$C_5$-$C_6$ cycloalkanols, such as aminocyclopentanol and aminocyclohexanol, or mixtures of these.

The diamino-$C_1$-$C_8$ alkanes (component c4) used are preferably diamino-$C_4$-$C_6$ alkanes, such as 1,4-diaminobutane, 1,5-diaminopentane or 1,6-diaminohexane (hexamethylenediamine, "HMD").

In one preferred embodiment for preparing the semiaromatic polyesters, use may be made of from 0.5 to 99.5 mol %, preferably from 0.5 to 50 mol %, of c3, based on the molar amount of B, and of from 0 to 50 mol %, preferably from 0 to 35 mol %, of c4, based on the molar amount of B.

The 2,2'-bisoxazolines c5 of the formula III are generally obtainable via the process of Angew. Chem. Int. Edit., Vol. 11 (1972), pp. 287-288. Particularly preferred bisoxazolines are those where $R^1$ is a single bond, $(CH_2)_z$-alkylene, where z=2, 3 or 4, for example methylene, ethane-1,2-diyl, propane-1,3-diyl or propane-1,2-diyl, or a phenylene group. Particularly preferred bisoxazolines which may be mentioned are 2,2'-bis(2-oxazoline), bis(2-oxazolinyl)methane, 1,2-bis(2-oxazolinyl)ethane, 1,3-bis(2-oxazolinyl)propane and 1,4-bis(2-oxazolinyl)butane, in particular 1,4-bis(2-oxazolinyl)benzene, 1,2-bis(2-oxazolinyl)benzene or 1,3-bis(2-oxazolinyl)benzene.

In preparing the semiaromatic polyesters use may, for example, be made of from 70 to 98 mol % of B, up to 30 mol % of c3 and from 0.5 to 30 mol % of c4 and from 0.5 to 30 mol % of c5, based in each case on the total of the molar amounts of components B, c3, c4 and c5. In another preferred embodiment, use may be made of from 0.1 to 5% by weight, preferably from 0.2 to 4% by weight, of c5, based on the total weight of A and B.

The component c6 used may be naturally occurring aminocarboxylic acids. These include valine, leucine, isoleucine, threonine, methionine, phenylalanine, tryptophan, lysine, alanine, arginine, aspartamic acid, cysteine, glutamic acid, glycine, histidine, proline, serine, tyrosine, asparagine and glutamine.

Preferred aminocarboxylic acids of the formulae IVa and IVb are those where s is a whole number from 1 to 1000 and t is a whole number from 1 to 4, preferably 1 or 2, and t has been selected from the group consisting of phenylene and —$(CH_2)_u$—, where u is 1, 5, or 12.

c6 may also be a polyoxazoline of the formula V. However, c6 may also be a mixture of different aminocarboxylic acids and/or polyoxazolines.

In one preferred embodiment, the amount of c6 used may be from 0.01 to 50% by weight, preferably from 0.1 to 40% by weight, based on the total amount of components A and B.

Among other components which may be used, if desired, for preparing the semiaromatic polyesters are compounds d1 which comprise at least three groups capable of ester formation.

The compounds d1 preferably comprise from three to ten functional groups which are capable of developing ester bonds. Particularly preferred compounds d1 have from three to six functional groups of this type in the molecule, in particular from three to six hydroxy groups and/or carboxy groups. Examples which should be mentioned are: tartaric acid, citric acid, maleic acid; trimethylolpropane, trimethylolethane; pentaerythritol; polyethertriols; glycerol; trimesic acid; trimellitic acid, trimellitic anhydride; pyromellitic acid, pyromellitic dianhydride, and hydroxyisophthalic acid.

The amounts generally used of the compounds d1 are from 0.01 to 15 mol %, preferably from 0.05 to 10 mol %, particularly preferably from 0.1 to 4 mol %, based on component A.

Components d2 used are an isocyanate or a mixture of different isocyanates. Aromatic or aliphatic diisocyanates may be used. However, higher-functionality isocyanates may also be used. For the purposes of the present invention, aromatic diisocyanate d2 is especially tolylene 2,4-diisocyanate, tolylene 2,6-diisocyanate, diphenylmethane 2,2'-diisocyanate, diphenylmethane 2,4'-diisocyanate, diphenylmethane 4,4'-diisocyanate, naphthylene 1,5-diisocyanate or xylylene diisocyanate. By way of example, it is possible to use the isocyanates obtainable as Basonat® from BASF Aktiengesellschaft.

Among these, particular preference is given to diphenylmethane 2,2'-, 2,4'- and 4,4'-diisocyanate as component d2. The latter diisocyanates are generally used as a mixture.

A three-ring isocyanate d2 which may also be used is tri(4-isocyanophenyl)methane. Multi-ringed aromatic diisocyanates arise during the preparation of single- or two-ring diisocyanates, for example.

Component d2 may also comprise subordinate amounts, e.g. up to 5% by weight, based on the total weight of component d2, of uretdione groups, for example for capping the isocyanate groups.

For the purposes of the present invention, an aliphatic diisocyanate d2 is primarily a linear or branched alkylene diisocyanate or cycloalkylene diisocyanate having from 2 to 20 carbon atoms, preferably from 3 to 12 carbon atoms, e.g. hexamethylene 1,6-diisocyanate, isophorone diisocyanate, or methylenebis(4-isocyanatocyclohexane). Hexamethylene 1,6-diisocyanate and isophorone diisocyanate are particularly preferred aliphatic diisocyanates d2.

Among the preferred isocyanurates are the aliphatic isocyanurates which derive from $C_2$-$C_{20}$, preferably $C_3$-$C_{12}$, cycloalkylene diisocyanates or alkylene diisocyanates, e.g. isophorone diisocyanate or methylenebis(4-isocyanatocyclohexane). The alkylene diisocyanates here may be either linear or branched. Particular preference is given to isocyanurates based on n-hexamethylene diisocyanate, for example cyclic trimers, pentamers, or higher oligomers of n-hexamethylene diisocyanate.

The amounts generally used of component d2 are from 0.01 to 5 mol %, preferably from 0.05 to 4 mol %, particularly preferably from 0.1 to 4 mol %, based on the total of the molar amounts of A and B.

Divinyl ethers d3 which may be used are generally any of the customary and commercially available divinyl ethers. Preference is given to the use of 1,4-butanediol divinyl ethers, 1,6-hexanediol divinyl ethers or 1,4-cyclohexanedimethanol divinyl ethers or a mixture of these.

The amounts of the divinyl ethers preferably used are from 0.01 to 5% by weight, especially from 0.2 to 4% by weight, based on the total weight of A and B.

Examples of preferred semiaromatic polyesters are based on the following components: A, B, d1; A, B, d2; A, B, d1, d2; A, B, d3; A, B, c1; A, B, c1, d3; A, B, c3, c4; A, B, c3, c4, c5; A, B, d1, c3, c5; A, B, c3, d3; A, B, c3, d1; A, B, c1, c3, d3; or A, B, c2. Among these, particular preference is given to semiaromatic polyesters based on A, B and d1, or A, B and d2, or on A, B, d1 and d2. In another preferred embodiment, the semiaromatic polyesters are based on A, B, c3, c4 and c5 or A, B, d1, c3 and c5.

The polyester described above can, if required, also contain fillers which can be incorporated during the polymerization process at any stage or subsequently, for example in the melt of the polyester. It is possible to add from 0 to 80% by weight of fillers, based on the polyester. Examples of suitable fillers are carbon black, starch, lignin powder, cellulose fibers, natural fibers such as sisal and hemp, iron oxides, clay minerals, ores, calcium carbonate, calcium sulfate, barium sulfate and titanium dioxide.

The polyester may comprise other additives which can be incorporated during the polymerization process at any stage or subsequently, for example in the melt of the polyester. It is possible to add from 0 to 80%, preferably from 0 to 5%, by weight of fillers, based on the polyester. Examples of suitable additives are stabilizers such as tocopherol (vitamin E), organic phosphorus compounds, mono-, di- and polyphenols, hydroquinones, diarylamines, thioethers, UV stabilizers; nucleating agents such as talc; and lubricants and mold release agents based on hydrocarbons, fatty alcohols, higher carboxylic acids, metal salts of higher carboxylic acids such as calcium and zinc stearate, and montan waxes. The polyester can additionally be colored in any desired way by adding organic or inorganic dyes.

The polyester is generally biodegradable. For the purposes of the present invention, a substance or a mixture of substances complies with the feature termed "biodegradable" if this substance or the mixture of substances has a percentage degree of biodegradation of at least 60% in at least one of the three processes defined in DIN V 54900-2 (preliminary standard, as at September 1998).

The result of the biodegradability is generally that the polyesters or polyester mixtures break down within an appropriate and demonstrable period. The degradation may be brought about enzymatically, hydrolytically, oxidatively, and/or via exposure to electromagnetic radiation, such as UV radiation, and is mostly predominantly caused by exposure to microorganisms, such as bacteria, yeasts, fungi, and algae. An example of a method of quantifying the biodegradability mixes polyester with compost and stores it for a particular time. By way of example, according to DIN EN 13432 or DIN V 54900-2, Method 3, $CO_2$-free air is passed through ripened compost during the composting process and the compost is subjected to a defined temperature profile. Biodegradability is defined here by way of the ratio of the net amount of $CO_2$ liberated from the specimen (after deducting the amount of $CO_2$ liberated by the compost without the specimen) to the maximum possible amount of $CO_2$ liberated by the specimen (calculated from the carbon content of the specimen), this ratio being defined as the percentage biodegradability. Even after a few days of composting, biodegradable polyesters or biodegradable polyester mixtures generally show marked signs of degradation, for example fungal growth, cracking, and perforation.

Other methods of determining biodegradability are described by way of example in ASTM D5338 and ASTM D6400.

The preparation of the semiaromatic polyesters is known per se or can take place by methods known per se.

The preferred semiaromatic polyesters may be characterized by a molar mass ($M_n$) in the range from 1000 to 100 000 g/mol, in particular in the range from 9000 to 75 000 g/mol, preferably in the range from 10 000 to 50 000 g/mol. The preferred semiaromatic polyesters may also be characterized by and by a melting point in the range from 60 to 170° C., preferably in the range from 80 to 150° C.

The polyester may be optionally mixed with other polymers, preferably with polylactic acid. The term "polylactide" as used herein includes polylactic acid and all copolymers and blends of polylactide homopolymers and copolymers and is abbreviated as PLA. PLA's polymer architecture can vary, and as a result, affect properties. The variation in architecture results from the different proportions of enantiomers of lactic acid, D(−) and L(+), that are used in the synthesis. These lactic acids can produce three types of lactides: D, L, and meso, for polymerization. PLA resins containing more than 93 percent of L-lactic acid units are semi-crystalline, while PLA with 50-93 percent content of L-lactic acid is strictly amorphous. The homopolymers poly(D-lactide) or poly(L-lactide) and high D- or L-copolymers have very regular structures and develop a crystalline phase. The presence of both meso and D-lactide forms produces imperfections in the crystalline structure, reducing the percent crystallinity. Polylactic acid is obtained, for example, from NatureWorks LLC, Minnetonka, Minn., U.S.A and called NatureWorks® 4020 or 4042D. PLA may be present in up to 60 wt %, preferably up to 50 wt %, based on the total mass of polyester and PLA. Preferably, PLA may be present in an amount of 10 to 60 wt %, preferably 30 to 50 wt %, based on the total mass of polyester and PLA. Such a mixture of a semiaromatic polyester and PLA is commerically available, for example Ecovio® L BX 8145 from BASF SE (mixture of semiarometic polyester Ecoflex® F BX 7011 from BASF with 45 wt % PLA (NatureWorks®)

The gel comprises a $C_1$ to $C_{10}$ carboxylic acid and a thickener. The $C_1$ to $C_{10}$ carboxylic acid usually comprises one to 10 carbon atoms. There may be one, two or three carboxylic acid groups present in the molecule. Preferably, the carboxylic acid is dissolved or emulsified, preferably dissolved, in a solvent, preferably in water. Preferably, the carboxylic acid is formic acid, acetic acid, oxalic acid, malic acid, tartaric acid, glycolic acid, lactic acid, citric acid, mandelic acid, or mixtures thereof. More preferably, the carboxylic acid is formic acid, acetic acid, lactic acid, oxalic acid, or mixtures thereof. Most preferred is formic acid.

The thickener may be any type of chemical or natural compound, which is generally used to increase the viscosity of a fluid. Examples for suitable thickeners are polysaccharides, proteins (for example casein, gelatin), synthetic polymers, preferably polysaccharides, or inorganic clays (such as silicic acids or layered silicates). The thickeners above may be used separately or as mixtures, respectively.

Synthetic polymers are for example polyvinyl alcohol, poly(meth)acrylic acid or their salts, polyacrylamide, polyvinyl pyrrolidone, polyethylene glycole, styrene-maleic acid anhydride copolymers or their salts.

Polysacchaarides are for example starch (natural or modified), modified cellulose (e.g. hydroxyethyl cellulose, hydroxypropyl methylcellulose, hydroxypropyl cellulose, ethylhydroxyethyl cellulose, carboxymethylcellulose, methylcellulose, microcrystalline cellulose (a partially depolymerized from of cellulose prepared by the hydrolysis of wood pulp with hydrochloric acid)), agar, pectin, alginate, or natural gums based on polysaccharides (e.g. locust bean gum, guar gum, gum arabic, carrageenan, xanthan gum, gellan gum). Preferably, the thickener comprises a natural starch or modified starch.

More preferably, the thickener is a natural starch. The polysaccharides, such as the natural or modified starch, are typically used in powdered form.

The term "natural starch" refers to the starch in the state before it is mixed with the other components of the gel according to the invention. The natural starch may react later on with the $C_1$ to $C_{10}$ carboxylic acid and form derivatives of the natural starch. Such reactions are known from Wolff et al., J. Am. Chem. Soc. 1957, 79, 3860-3862 or from Gottlieb et al., J. Am. Chem. Soc. 1940, 62, 3342-3344.

e Natural starch, commonly called unmodified starch or pearl starches, may be produced by the wet milling and is commercially available in large industrial quantities as starch flour. Examples of natural starches are selected from the group consisting of corn starch, potato starch, wheat starch, rice starch, tapioca starch, sago starch, sorghum starch, cassaba starch, pea starch and mixtures of the stated natural starches. The natural starch may also be pregelatinized. Preferably, the unmodified starch is corn starch.

Suitable modified starches are hydrolytically or enzymatically degraded starches, for example dextrins, such as white or yellow dextrins and maltodextrins, or oxidized starches, such as dialdehyde starch. Further examples are starches esterified with inorganic or organic acids, in particular phosphated and acetylated starches, and starches etherified with organic halogen compounds, epoxides or sulfates, are also suitable. Starches and processes for their degradation and their chemical modification are described in Ullmann's Encyclopedia of Industrial Chemistry, 5th edition, Vol. A25, page 2 et seq., which is hereby incorporated by reference.

The gel may additionally comprises a sugar. The sugar may be any known monosaccharide or disaccharide or mixtures thereof, preferably those which are available from natural sources. Examples are saccharose (sucrose), glucose, lactose, fructose, dextrose, maltose. Technical mixtures comprising sugar may also be used, such as black sugar, brown sugar, honey, molasses. Preferably, the sugar is a disaccharide, more preferably saccharose.

The gel may additionally comprises an essential oil. An essential oil is understood to comprise oils extractable from plant or the essential component thereof which sometimes happens to be solid. Examples for essential oils are monoterpenes like menthol, geraniol, thymol, myrcene, citral, limonene, carene, camphor, eugenol, or cineol (eucalyptol); natural oils like oil from lemon, wintergreen, eucapyptus, neem, spearmint, cinnamon. The concentration of the essential oil in gel is not critical, but reasonably is between 1 and 50 wt % of the total weight of the gel. Preferably, the concentration is between 10 wt % and 40 wt %.

The gel comprises typically 15 to 85 wt % pure $C_1$ to $C_{10}$ carboxylic acid, more preferably 35 to 65 wt %, even more preferably 45 to 55 wt %, based on the total weight of the gel. The gel comprises typically 1 to 50 wt % thickener, more preferably 5 to 40 wt %, even more preferably 20 to 30 wt %, based on the total weight of the gel. In case the thickener comprises moisture, the concentration refers to the dry weight of the thickener. The gel comprises optionally up to 50 wt % sugar, more preferably up 30 wt %, even more preferably up 20 wt %, based on the total weight of the gel. In another embodiment the gel comprises optionally 1 to 50 wt % sugar, more preferably 3 to 30 wt %, even more preferably 10 to 20 wt %, based on the total weight of the gel. The gel typically comprises water, preferably up to 100 wt %, based on the total weight of the gel.

The gel may comprise further components, such as formulation additives. Examples are solvents, sugars, dyes, dispersants or emulsifiers (such as solubilizers, protective colloids, surfactants), bactericides, anti-freezing agents or anti-foaming agents.

The agrochemical compositions may also comprise auxiliaries which are customary in agrochemical compositions. The auxiliaries used depend on the particular application form and active substance, respectively. Examples for suitable auxiliaries are solvents, solid carriers, dispersants or emulsifiers (such as further solubilizers, protective colloids, surfactants and adhesion agents), bactericides, anti-freezing agents, coloring agents, or anti-foaming agents.

Suitable solvents are water, organic solvents such as mineral oil fractions of medium to high boiling point, such as kerosene or diesel oil, furthermore coal tar oils and oils of vegetable or animal origin, aliphatic, cyclic and aromatic hydrocarbons, e.g. toluene, xylene, paraffin, tetrahydronaphthalene, alkylated naphthalenes or their derivatives, alcohols such as methanol, ethanol, propanol, butanol and cyclohexanol, glycols, ketones such as cyclohexanone and gamma-butyrolactone, fatty acid dimethylamides, fatty acids and fatty acid esters and strongly polar solvents, e.g. amines such as N-methylpyrrolidone. Preferred solvent is water.

Suitable surfactants (adjuvants, wtters, tackifiers, dispersants or emulsifiers) are alkali metal, alkaline earth metal and ammonium salts of aromatic sulfonic acids, such as ligninsulfonic acid (Borresperse® types, Borregard, Norway) phenolsulfonic acid, naphthalenesulfonic acid (Morwet® types, Akzo Nobel, U.S.A.), dibutylnaphthalene-sulfonic acid (Nekal® types, BASF, Germany), and fatty acids, alkylsulfonates, alkylarylsulfonates, alkyl sulfates, laurylether sulfates, fatty alcohol sulfates, and sulfated hexa-, hepta- and octadecanolates, sulfated fatty alcohol glycol ethers, furthermore condensates of naphthalene or of naphthalenesulfonic acid with phenol and formaldehyde, polyoxy-ethylene octylphenyl ether, ethoxylated isooctylphenol, octylphenol, nonylphenol, alkylphenyl polyglycol ethers, tributylphenyl polyglycol ether, tristearylphenyl polyglycol ether, alkylaryl polyether alcohols, alcohol and fatty alcohol/ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and proteins, denatured proteins, polysaccharides (e.g. methylcellulose), hydrophobically modified starches, polyvinyl alcohols (Mowiol® types, Clariant, Switzerland), polycarboxylates (Sokolan® types, BASF, Germany), polyalkoxylates, polyvinylamines (Lupasol® types, BASF, Germany), polyvinylpyrrolidone and the copolymers thereof.

Bactericides may be added for preservation and stabilization of the composition. Examples for suitable bactericides are those based on dichlorophene and benzylalcohol hemi formal (Proxel® from ICI or Acticide® RS from Thor Chemie and Kathon® MK from Rohm & Haas) and isothiazolinone derivatives such as alkylisothiazolinones and benzisothiazolinones (Acticide® MBS from Thor Chemie). Examples for suitable anti-freezing agents are ethylene glycol, propylene glycol, urea and glycerin. Examples for anti-foaming agents are silicone emulsions (such as e.g. Silikon® SRE, Wacker, Germany or Rhodorsil®, Rhodia, France), long chain alcohols, fatty acids, salts of fatty acids, fluoroorganic compounds and mixtures thereof.

Examples of a coloring agent is a dye or a pigment, such as Rhodamin B, C.I. Pigment Red 112, C.I. Solvent Red 1, pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108, amaranth, amaranth aluminium lake, erythrosine, erythrosine aluminium lake, new coccine, Chlorine, rose Bengal, acid eyed, tetrazzini, tetrazzini aluminium lake, Sunset Yellow FCF, Sunset Yellow FCF aluminium lake, Fast Green FCF, Fast Green FCF aluminium lake, Brilliant Blue FCF, Brilliant Blue FCF aluminium lake, indigo carmine, indigo carmine aluminium lake, beta-carotene, copper chlorophyll.

The present invention further relates to a gel according to the invention. The gel corners the $C_1$ to $C_{10}$ carboxylic acid and the thickener as described above.

A method for preparing the dispenser according to the invention comprising
a) mixing the $C_1$ to $C_{10}$ carboxylic acid and the thickener, and
b) filling the mixture of step a) into the dispenser.

Preferably, step a) comprises mixing the thickener at a temperature below 35° C. with the $C_1$ to $C_{10}$ carboxylic acid.

Preferably, step a) comprises
a1) mixing the $C_1$ to $C_{10}$ carboxylic acid and the sugar, and
a2) adding to the mixture of a1) the thickener.

For easier filling the mixture into the dispenser in step b), the mixture may be warmed up to 90° C., preferably up to 60° C.

The mixture of step a) comprises typically 15 to 85 wt % pure $C_1$ to $C_{10}$ carboxylic acid, more preferably 35 to 65 wt %, even more preferably 45 to 55 wt %, based on the total weight of the mixture resulting in step a). The $C_1$ to $C_{10}$ carboxylic acid may be added as pure compound or, preferably, as aqueous solution. More preferably, the $C_1$ to $C_{10}$ carboxylic acid is added as 70 to 99 wt %, more preferably 80 to 97 wt % aqueous solution of formic acid.

The mixture of step a) comprises typically 1 to 50 wt % thickener, more preferably 5 to 40 wt %, even more preferably 20 to 30 wt %, based on the total weight of the mixture resulting in step a). In case the thickener comprises moisture, the concentration refers to the dry weight of the thickener.

The mixture of step a) comprises optionally 1 to 50 wt % sugar, more preferably 3 to 30 wt %, even more preferably 10 to 20 wt %, based on the total weight of the mixture resulting in step a).

The mixture of step a) comprises typically up to 100 wt % water, based on the total weight of the gel.

The present invention further relates to a method for the control of mites in bee hives comprising putting the dispenser according to the invention inside or near, preferably inside, a bee hive. The term "bee hive" corresponds to all arrangements, which are used for keeping bees (including mating nukes for queens). The application timing will be based on established Integrated Pest Management principles. The preferred application timing is during the honey flow (e.g. when supers (wooden boxes for storing honey storage) are on the hives). Usually, an amount of 10 to 500 g gel, preferably 50 to 300 g, is used per treatment and per hive. The amount depends on the size of the hive and can easily adopted by an expert as required.

The present invention also relates to a use of the dispenser according to the invention for the control of mites in bee hives.

The present invention also relates to a use of the dispenser according to the invention or the gel according to the invention for the control of mites in agricultural, industrial or domestic environment.

The present invention further relates to a method for the control of nosegay in bee hives comprising putting the dispenser according to the invention inside or near, preferably inside, a bee hive. The application timing will be based on established Integrated Pest Management principles. Nosegay (also called osmosis) is a well known disease in beekeeping. Infections of nosegay are often caused by a microsporidian Nosema apis or Nosema ceranae (Bourgeois et al., Journal of Invertebrate Pathology, 2010, 103, 53-58). It is known from WO 2005/110384 to control nosema in honey bees for example with compositions comprising acetyl-salicylic acid or the antibiotic fumagillin.

The present invention also relates to a use of the dispenser according to the invention for the control of nosea in bee hives.

The present invention also relates to a use of the dispenser according to the invention or the gel according to the invention for the control of nosea in agricultural, industrial or domestic environment.

Advantages of the present invention are that it distinctively increases the health of bee colonies. For example varroa mites can be controlled effectively. The dispenser can be handled easily by the beekeeper, because the corrosive formic acid is well protected inside the dispenser. Because of the particular polyester membrane which allows the controlled diffusion of the formic acid, no hole punching or cutting slits into formic acid pads is required to release the formic acid. Another advantage of the invention is that it may be applied all year round, even in hot summer months. The gel is non-toxic to bees. The device and/or the gel is biodegradable. Yet another advantage is to avoid antibiotics for the treatment of nosema.

The inventive examples below give further illustration of the invention, which is not, however, restricted to these examples.

EXAMPLES

Example 1

Preparation of a Formic Acid Gel

A formic acid solution (56.9 parts by weight of a 85 wt % aqueous solution; corresponding to 48.4 parts by weight pure formic acid) was warmed to 40-50° C. Granulated sucrose (16.1 parts by weight) was added and stirred until dissolved. The formic acid/sucrose solution was cooled. Powdered corn starch (27.0 parts by weight; moisture content 10 wt %) was added (and optionally a food dye) and mixed. The solution was chilled until a paste was formed.

Example 2

Preparation of a Pouch

The paste as prepared in Example 1 was then metered (50, 100, 150 or 200 g) and poured or pumped into a permeable membrane pouch. A vapour permeable membrane pouch is used to encase the gel. The pouch was sealed and the paste press-formed into a strip. The strips were wrapped in an outer pouch and placed in an HDPE pail for storage. At room temperature a very stiff, translucent gel will form, essentially a solid. If it is liquefied by heat (e.g. up to 100° C.), it returned to a stiff gel at room temperature.

The pouch was made of a biodegradable polyester membrane, which was made of a aliphatic-aromatic copolyester (polycondensate of 1,4-butanediol, adipic acid and terephthalic acid; melting point 110-120° C. as determined by DSC; tensile strength 34 N/mm$^2$ as determined by ISO 527; ultimate elongation (MD) 560% as determined by ISO 527; water permeation rate 140 g/(m$^2$*d) as determined by DIN 53122). The film thickness of the membrane was 32 μm.

Example 3

Field Trials (Florida)

A trial for efficacy and colony health in 34 honey bee colonies was made in Gainesville, Florida in March to April 2009 with a one month follow-up evaluation period after the treatment application.

When the colonies received a single 200 gram pouch (prepared as in Example 2) within the cluster area the level of the varroa mites was knocked down to well below treatment threshold and stayed that way. No further treatments were projected to be required for a minimum of 4 months. The colony health did not appear to be affected in any way.

The formic acid was diffused from the pouch into the colony area at a rate such that by the end of 72 hours it had dropped to a 10 wt % concentration from the initial 48.4 wt %. The delivery system was completely compostable and the bees initiated removal by chewing. The beekeeper had removed the spent product without risk to his health.

Example 4

Field Trials (Canada)

A trial for stress and colony health in 12 bee colonies was made in Frankford, Ontario in May 2009. Up to three times a 200 g pouch (prepared as in Example 2) was applied to the colonies. Entrance reducers were on for the first 24 hours on the treated colonies, and then removed. Seven hives in the test had 1.5, 2 and 3 times the 200 gram treatment applied, plus one at the 200 gram level with no entrance reducer. Four colonies were untreated controls with no entrance reducers.

The queens were all fine. Some minor brood damage and adult bee mortality occurred at the higher amounts, but that may have been moderated if the entrance reducers had been off from the start of the trial. The strength of the colony did not have an effect on the results.

Examination of the Drone Brood one week after application: A comb with capped drone brood is laid on a flat, clean surface. With a cappings fork the capped drone larva was stabbed horizontally and lifted out. The larva appeared to be healthy. Sometimes dead varroa would be seen on the pupae. When the frame would be slowly turned so the side where the drone larva had been pulled out was now facing down toward the flat surface and given a sharp shake, dead varroa would fall out. Some of them were just empty shells.

Phoretic Varroa: An alcohol wash (3 frames with brood from the center of the brood nest shaken into a tub, 200-300 bees per sample, 12 colonies) was performed on the colonies in the trial. None of the treated colonies came up with any varroa after the treatment. For comparison, varroa mites were present in the alcohol washes of the control hives.

The formic fudge formulation, when tested at up to three time the likely to be recommended dose of 200 g, did not succeed in killing the queens, even with the entrances reduced to the over-wintering size for the first 24-hours. The varroa mites appeared to be highly susceptible to the treatment when phoretic and on the pupating drones.

Example 5

Field Trials (France)

39 hives (3 apiaries of each 13 hives with 4 to 5 hives per modality and about 35.000 bees per hive) were selected for this trial, which was conducted in France from August to October. Main adjacent flowering crops were alfalfa. The formic acid pouches were applied in two modalities: inside hives equipped with a super, and inside hives without super. In these two modalities three pouches of each 100 g (total dose 300 g) were set on the top of the combs on day zero (D0) and then removed three days later (D+3). In each of the apiary four to five hives were used as a control. They were not treated with pouches but conducted in the same conditions for the purpose of comparisons. These colonies induced data that validated the trial performance.
Description and identification of the modalities:
Modality No. 1: control hives without super (not according to the invention)
Modality No. 2: treated hives with super (3 pouches per hive)
Modality No. 3: treated hives without super (3 pouches per hive)

During the 28 days after the application of pouches in the hives, no adverse effects were found on the colony strength and the development.

A) Evaluation of the Varroa Mortality

The mortality of the Varroa mites was evaluated with the method of counts on sticky boards. Records are carried out at D−3, D0 (day of the application of pouches), D+3, D+7, D+10, D+13, D+16, D+19 and D+22 (see table 1). In the untreated modality (#1) the number of mites on sticky boards remained quite stable from D0 to D+22. In the treated modalities (#2 and 3) the application of the pouches at D0 induces a Varroa mortality peak at D+3. The effect on the Varroa mortality continues until D+13. At the end of the trial (D+22), the average Varroa mortality of the two treated modalities was under the untreated one. For the modality "with super" (#2), the Varroa mortality is higher than the one recorded in the modality "without super" (#3) in two of the three apiary. The presence of a super on the hives seems to increase the efficacy of the test item. It may be explained by the increase of contacts of bees with the pouch as they are set between the hive and the super.

Sticky board method: A board was covered with grease and set up, sticky face above, under the specific hive floor for Varroa mites counts (grid floor). The board is slid out after 3-4 days and naturally felt mites were directly counted and removed.

TABLE 1

Average varroa felt determined by sticky board method

| Date | Modality 1[a] | Modality 2 | Modality 3 |
|---|---|---|---|
| D − 3 | 4.3 | 5.3 | 4.4 |
| D − 3 | 13.9 | 22.8 | 17.3 |
| D0 | 43.9 | 39.9 | 39.9 |
| D + 3 | 43.3 | 568.2 | 488.6 |
| D + 7 | 46.0 | 183.9 | 181.6 |
| D + 10 | 54.0 | 135.6 | 93.9 |
| D + 13 | 38.4 | 112.3 | 75.6 |
| D + 16 | 79.0 | 54.7 | 50.5 |
| D + 19 | 30.2 | 36.8 | 66.5 |
| D + 22 | 47.0 | 18.8 | 26.0 |
| D + 28 | 10.6 | 0.5 | 1.1 |

[a]control modality, not according to the invention.

B) Infestation Levels

Infestation levels of bees were evaluated with the alcohol wash method at D−3 and D+28 (Table 2). The infestation was increasing in the untreated modality from an average of 4 to 10% bees infected. The efficacy excellent in modality 2 "with super" (average 96.5% efficacy) and in the modality 3 "without super" α-verage 89.5% efficacy). The efficacy (%) was calculated with Henderson and Tilton formula: $100 \times (1-(Pt \times Ta)/(Pa \times Tt))$, wherein Pa=% infestation in the treated modality before application; Pt=% infestation in the treated modality after application; Ta=% infestation in the untreated modality before application; Tt=% infestation in the untreated modality after application.

Alcohol wash method: The hive was opened and a full cup of adult bees was sampled (about 300 bees) and put into a jar half fill with an alcohol solution at about 50%. The jar was gently shook then the content was filtered in a strainer in order to retain bees. Mites passed through the strain then were retained on the fine net mesh to be counted.

TABLE 2

Average infestation levels determined by alcohol wash method

| Date | Modality 1[a] | Modality 2 | Modality 3 |
|---|---|---|---|
| D − 3 | 4.3 | 5.3 | 4.4 |
| D + 28 | 10.6 | 0.5 | 1.1 |
| Efficacy [%] | 0.0 | 96.5 | 89.5 |

[a]control modality, not according to the invention.

C) Varroa in Brood

Three days after the application (D+3) brood specimens were sampled from each hive in order to assess the number of Varroa mites per bee larvae and per drone larvae. Unfortunately, due to the late season (August), drone brood was reduced or lacked. Mean data are presented in table 3.

In the untreated modality (#1), counts on brood specimens showed the same number of living or dead Varroa mites per 100 bee larvae (5.1 and 5.6 respectively) and it showed slightly more living than dead Varroa on drone larvae (1.9 and 0.4 respectively).

In treated modalities (#2 and 3), a lot more dead Varroa mites were observed on bee larvae: about 21 dead mites per 100 bee larvae and 1 alive in the modality "with super" and about 11 dead mites per 100 bee larvae in the modality "without super". Concerning the drone larvae, about two times more dead mites than alive are observed.

TABLE 3

Mean number of Varroa mites on bee and drone brood

| | | Modality | | |
|---|---|---|---|---|
| | | 1[a] | 2 | 3 |
| Per 100 Bee larvae | Dead | 5.1 | 21.6 | 11.6 |
| | Alive | 5.6 | 1.0 | 1.2 |
| Per 20 drone larvae | Dead | 0.4 | 3.1 | 2.2 |
| | Alive | 1.9 | 1.3 | 1.2 |

[a]control modality, not according to the invention.

D) Nosema Analysis 25 forager bees per modality were picked up just in front of the hive on the day of application (D0) and three days after application (D+3). The bees were frozen until nosema spore analysis. The spore level of the treated hives was much lower for both Modality No. 2 and Modality No. 3 compared to the untreated control hives of Modality No. 1.

The invention claimed is:

1. A dispenser, comprising:
   a polyester membrane; and
   a gel disposed within the polyester membrane, the gel comprising a $C_1$ to $C_{10}$ carboxylic acid and a thickener, wherein the polyester membrane comprises a semiaromatic copolyester, wherein the thickener is a natural starch and wherein the gel comprises at least 3 wt % sugar, wherein the sugar is selected from the group consisting of monosaccharide, disaccharide, and mixtures thereof.

2. The dispenser of claim 1, wherein the dispenser is a pouch.

3. The dispenser of claim 1, wherein the gel comprises at least 5 wt % thickener.

4. The dispenser of claim 1, wherein the semiarmoatic copolyester comprises 1,4-butanediol, adipic acid and terephthalic acid in polymerized form.

5. The dispenser of claim 1, wherein the polyester membrane is attached to a coating substrate.

6. The dispenser of claim 1, wherein the $C_1$ to $C_{10}$ carboxylic acid is formic acid, acetic acid, oxalic acid, malic acid, tartaric acid, glycolic acid, lactic acid, citric acid, mandelic acid, or mixtures thereof.

7. A method for preparing the dispenser of claim 1, comprising
   a) mixing the $C_1$ to $C_{10}$ carboxylic acid and the thickener to form a gel, and
   b) placing the gel of step a) into the dispenser.

8. The method according to claim 7, wherein step a) comprises mixing the thickener at a temperature below 30° C. with the $C_1$ to $C_{10}$ carboxylic acid.

9. A method for the control of mites in bee hives comprising providing the dispenser of claim 1, and placing the dispenser inside or near a bee hive.

10. A method for the control of nosema in bee hives comprising providing the dispenser of claim 1, and placing the dispenser inside or near a bee hive.

11. The method of claim 9, wherein the thickener is a polysaccharide.

12. The method of claim 9, wherein the dispenser is a pouch.

13. The method of claim 9, wherein the gel comprises at least 5 wt % thickener.

14. The method of claim 9, wherein the semiarmoatic copolyester comprises 1,4-butanediol, adipic acid and terephthalic acid in polymerized form.

15. The method of claim 9, wherein the $C_1$ to $C_{10}$ carboxylic acid is selected from the group consisting of formic acid, acetic acid, oxalic acid, malic acid, tartaric acid, glycolic acid, lactic acid, citric acid, mandelic acid, and mixtures thereof.

16. The method of claim 10, wherein the dispenser is a pouch.

17. The dispenser of claim 1, wherein the gel comprises from 15 to 85 wt % of the $C_1$ to $C_{10}$ carboxylic acid.

18. The dispenser of claim 1, wherein the gel comprises at least 20 wt % of the thickener.

19. The dispenser of claim 1, wherein the $C_1$ to $C_{10}$ carboxylic acid is selected from the group consisting of formic acid, acetic acid, lactic acid, oxalic acid, and mixtures thereof.

20. The dispenser of claim 1, wherein the dispenser is a pouch having a volume of 30 to 1000 ml.

21. The dispenser of claim 1, wherein the polyester membrane has a thickness of 10 to 200 µm.

* * * * *